United States Patent
Kaplan

(10) Patent No.: US 6,441,248 B1
(45) Date of Patent: Aug. 27, 2002

(54) PREPARATION OF BIPHENOLS BY OXIDATIVE COUPLING OF ALKYLPHENOLS USING COPPER CATALYST

(75) Inventor: Gregory Kaplan, Bexley, OH (US)

(73) Assignee: Wiley Organics, Inc., Coshocton, OH (US)

( * ) Notice: Subject to any disclaimer, the term of this patent is extended or adjusted under 35 U.S.C. 154(b) by 0 days.

(21) Appl. No.: 09/511,029

(22) Filed: Feb. 23, 2000

(51) Int. Cl.$^7$ ............................................. C07C 37/00
(52) U.S. Cl. ...................................................... 568/730
(58) Field of Search ........................................ 568/730

(56) References Cited

U.S. PATENT DOCUMENTS

| | | | |
|---|---|---|---|
| 4,100,202 A | 7/1978 | Rutledge | 568/730 |
| 4,130,504 A | 12/1978 | Rutledge | 252/430 |
| 4,156,788 A | 5/1979 | Earley | 568/730 |
| 4,195,189 A | 3/1980 | Earley | 568/730 |
| 4,205,187 A | 5/1980 | Cardenas et al. | 568/730 |
| 4,238,627 A | 12/1980 | Reichle | 568/730 |
| 4,410,736 A | 10/1983 | Strom | 568/730 |
| 4,482,754 A | 11/1984 | Strom | 568/730 |
| 4,482,755 A | 11/1984 | Kruse et al. | 568/730 |
| 4,487,722 A | 12/1984 | Everly et al. | 260/465 F |
| 4,487,977 A | 12/1984 | Kruse et al. | 568/730 |
| 4,487,978 A | 12/1984 | Kruse et al. | 568/730 |
| 4,851,589 A | 7/1989 | Cliffton et al. | 568/730 |
| 4,902,837 A | 2/1990 | Tanaka et al. | 568/730 |
| 4,965,384 A | 10/1990 | Cliffton et al. | 556/110 |
| 6,077,979 A * | 6/2000 | Qui | 568/730 |

* cited by examiner

*Primary Examiner*—Peter O'Sullivan
(74) *Attorney, Agent, or Firm*—Thompson Hine LLP

(57) ABSTRACT

This invention relates to a method for producing biphenols by oxidative coupling of dialkylphenols which proceeds in two stages using a copper amine complex which is catalytically effective in each stage.

10 Claims, No Drawings

PREPARATION OF BIPHENOLS BY OXIDATIVE COUPLING OF ALKYLPHENOLS USING COPPER CATALYST

BACKGROUND OF THE INVENTION

The invention relates to a method for producing biphenols by oxidative coupling of dialkylphenols. More particularly it is directed to a method which proceeds in two stages using a copper amine complex which is catalytically effective in each stage. Still more particularly it relates to a novel copper amine complex with high catalytic activity for the oxidative coupling of substituted phenols under mild conditions which has dual (two stage) activity and can be readily recycled and reused.

SUMMARY OF THE INVENTION

The invention is a process for producing tetraalkylbiphenols and, more particularly, 2,2',6,6'-tetraalkyl-4,4'-biphenols by the stepwise oxidative coupling of 2,4-dialkylphenols or 2,6-dialkylphenols in the presence of a copper amine complex. The reaction of the 2,6-dialkylphenones is preferred. The first step of this reaction is the synthesis of 3,3',5,5'-tetraalkyl-4,4'-diphenoquinones using oxygen as an oxidizer-to couple the 2,6-dialkylphenols. The second step is the synthesis of 2,2',6,6'-tetraalkyl-4,4'-biphenols using 3,3',5,5'-tetraalkyl-4,4'-diphenoquinones as an oxidizer to couple 2,6-dialkylphenols. (Both steps usually employ an excess of the phenol.) In accordance with the invention, the same catalyst can be used in both steps. In addition, the reaction proceeds under extremely mild conditions used in the preferred embodiments of the invention and this results in highly selective syntheses in both steps. Thus in the first step of the preferred process only 3,3',5,5'-tetraalkyl-4,4'-diphenoquinones are produced, and in the second step only 2,2',6,6'-tetraalkyl-4,4'-biphenols are produced. Low temperature prohibits dealkylation of biphenols, which results in impurities such as polyphenols.

The reaction of the 2,4-dialkylphenones proceeds directly to the 2,2'-diphenol and does not proceed via the diphenoquinone.

The extremely high activity of the catalytic system used in the preferred embodiment of the invention enables the use of only a very modest amount (i.e. about 0.05 to 1% based on dialkylphenol) of catalyst. In addition, the oxidation proceeds well at modest concentrations of oxygen; thus headspace air pressures as low as 1 to 100 psi are useful and high pressures for oxygenation are not required. The catalyst is readily removed from the product stream and recovered for reuse. Typically, essentially no impurities are produced. The system described below also can permit the efficient recovery of any unreacted 2,6-dialkylphenol starting materials, permitting their reuse without subsequent additional purification.

With specific reference to the reaction of 2,6-dialkylphenol, it has been discovered that 2,2',6,6'-tetraalkyl-4,4'-biphenols can be efficiently produced in a two-step process by using a copper-amino salt complex with dual catalytic activity and two oxidizing agents, first oxygen, then the corresponding 3,3',5 '-tetraalkyl-4,4'-diphenoquinone intermediate, to couple 2,6-dialkylphenols. The process utilizes a solvent, which significantly reduces the temperature at which the coupling occurs, permitting high selectivity to be achieved. In addition, the solvent permits the recovery of excess 2,6-dialkylphenol and catalyst for reuse without subsequent additional purification.

The catalyst has improved catalytic activity compared to a similar system described in U.S. Pat. No. 4,851,589. Unlike the catalyst described in that patent, the catalyst preferably used in the present invention, does not require an activation period, the use of acidic phenols, and can be removed from the products while retaining its full activity and reused. In addition, the catalyst can be prepared, recovered and stored in closed containers for over one year while retaining full catalytic activity, eliminating the need to prepare fresh catalyst for each reaction.

In accordance with another embodiment of the invention, tetraalkylbiphenols are dealkylated to produce a 4,4'-biphenol and its analogs. In a preferred embodiment, this reaction is conducted in the presence of a low boiling solvent to enhance and facilitate the removal of isobutylene and prevent the formation of polyisobutylene.

DETAILED DESCRIPTION OF THE INVENTION

In accordance with the preferred embodiments of the invention, the catalyst is prepared by reacting a copper halide (e.g., cuprous bromide, cupric chloride, cupric bromide, and preferably cuprous chloride (CuCl)), with a tetraalkylalkylenediamine. The preferred diamine is N,N,N',N'-tetramethyletylenediamine (TMEDA) but other diamines that have been used in the preparation of copper amine complexes could also be used such as alkylamines, dialkylamines, arylamines, pyridines etc. In the preferred embodiment of the invention the copper-amino complex is prepared under aerobic conditions in the polar organic solvents such as acetone, tetrahydrofuran (THF), alkyl esters such as ethyl acetate, butyl acetate etc., other ketones such as methyl ethyl ketone (MEK), etc., and ethers such as dimethyl ether, methyl-t-butyl ether (MTBE), etc. These solvents are selected because the catalyst is essentially insoluble and precipitates as a dark brown solid. The catalyst clearly differs in its properties from the catalyst described in the U.S. Pat. No. 4,851,589. It is prepared in a different solvent resulting in precipitation and the dark brown solid that is recovered cannot be completely dissolved in methanol or ethanol. In addition, it can be readily removed from the products of the reaction while retaining its activity, permitting it to be re-used in subsequent reactions. In the presence of oxygen it converts 2,6-dialkylphenols to 3,3',5,5'-tetraalkyl-4,4'-diphenoquinones. Under the conditions described herein, the diphenoquinones are typically produced exclusively and not as a mixture of 3,3',5,5'-tetraalkyl-4,4'-diphenoquinones and 2,2',6,6'-tetraalkyl-4,4'-biphenols which typifies other processes. The same catalyst catalyzes the oxidative coupling of the dialkylphenol and the reduction of the diphenoquinones in the second stage of the reaction.

The invention is not limited to the use of the preferred copper-amino complex. Known copper-amino complexes can also be adapted for use in the two stage dual catalytic reaction of 2,6-dialkylphenols as described herein.

Process Conditions

In a typical process in accordance with the present invention, the 2,6-dialkylphenol to be coupled is dissolved in methanol. While methanol is clearly the preferred solvent, those skilled in the art will recognize that other solvents, in particular other alcohols such as ethanol, isopropanol or butanol can be used. A solvent is selected which dissolves the dialkylphenol and the catalyst and water. It is also important to be able to remove water from this solvent, if it is to be reused in the next cycle. In addition to alcohols ketones may also be useful. The concentration of the 2,6-dialkylphenol is typically about 1 to 5 molar.

An excess of the phenol is used for the reaction. As little as 0.05% by weight of catalyst based on phenol can be effective and is added to the solution of the phenol. The preferred catalyst is completely soluble in the methanolic solution of the 2,6-dialkylphenol. Oxygen or air is bubbled directly into reaction mixture, or is delivered to the headspace of the reactor at a modest pressure (i.e., about 5 to 20 psi air). The amount of oxygen is readily determined based on the stoichiometry of the reaction. The temperature of the reaction can be easily and preferably controlled in the range of about 30 to 50° C. Higher temperatures can be used particularly with solvents having a higher boiling point than methanol but in the interest of maintaining the selectivity of the reaction lower temperatures are preferred. Methanol serves several of important purposes: it keeps the viscosity of the reaction mixture low while the 3,3',5,5'-tetraalkyl-4,4'-diphenoquinones are being produced, affording ease of agitation and efficient mixing; it freely dissolves water, the byproduct of reaction, keeping the catalyst active; methanol is also used to separate the catalyst and excess 2,6-dialkylphenol from the final product for reuse in subsequent reactions.

Typically after approximately 35 to 40% of initial 2,6-dialkylphenols have been converted to the corresponding 3,3',5,5'-tetraalkyl-4,4'-diphenoquinones, oxygen addition may be stopped and reaction carried out in the absence of oxygen. At this time the methanol solvent is removed by distillation for re-use, then the water produced as a by-product of the reaction is removed by distillation at a higher temperature and disposed of. For the second stage reaction, the temperature needs to be raised just enough to keep reaction mixture in a liquid form, typically about 130 to 160° C. The presence of the catalyst permits the intermediate 3,3',5,5'-tetraalkyl-4,4'-diphenoquinones to serve as oxidizing agents, for the subsequent coupling of the 2,6-dialkylphenols. Higher temperatures may be used if higher concentrations of diphenoquinone are used but it is not desirable to exceed temperatures of 200° C. because catalyst will thermally decompose and dealkylation may occur. After the 3,3',5,5'-tetraalkyl-4,4'-diphenoquinone is consumed, the reaction mixture generally contains about 70 to 80% 2,2',6,6'-tetraalkyl-4,4'-biphenols and 20 to 30% 2,6-dialkylphenols. The reaction mixture is then cooled to approximately 60° C. and the methanol that was removed by distillation is added back to the reaction mixture. In a period of several minutes the 2,2',6,6'-tetraalkyl-4,4'-biphenols precipitate completely and can be removed by filtration or centrifugation, while the 2,6-dialkylphenols and the active catalyst remain in the filtrate or centrate. Following the addition of fresh 2,6-dialkylphenol and optional addition of fresh catalyst, these mother-liquors can be re-used to start another cycle of producing of 2,2',6,6'-tetraalkyl-4,4'-biphenols.

The 2,6-dialkylphenols which can be reacted in accordance with the invention are represented by formula:

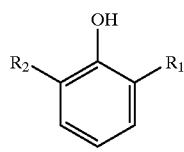

where $R_1$ is an alkyl group having 1 to 6 carbons, and $R_2$ is alkyl group having 3 to 6 carbons. In order to prevent coupling through the oxygen atom and production of a mixture of C—O coupled oligomers, one of the alkyl groups should have at least three carbon atoms to provide steric hindrance with respect to the phenolic oxygen atom and thereby prevent reaction. While the principal focus of the invention is on the preparation of tetraalkylbiphenols, R1 and R2 could also be C1 to C6 alkoxy moeities.

The reaction of the 2,6-dialkylphenol is shown in the following equations:

Step 1:

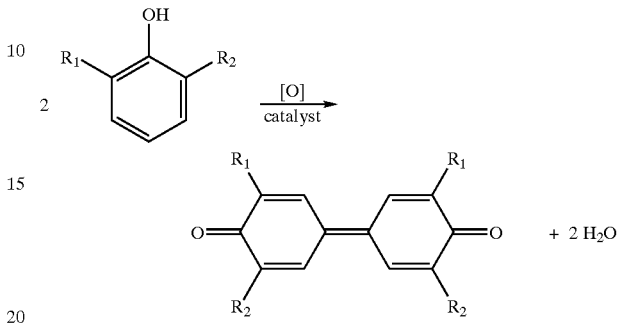

Step 2:

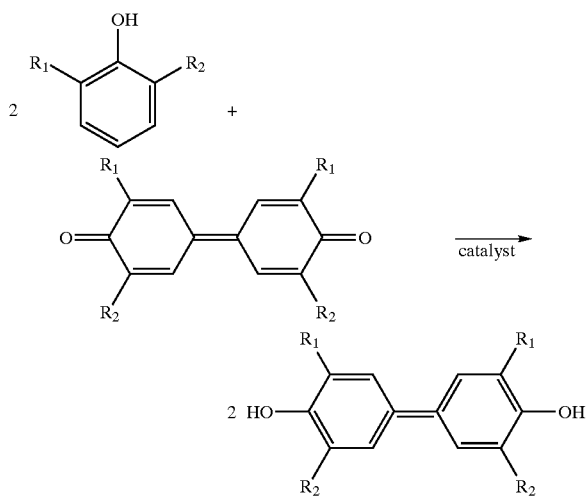

The catalytic system described in this patent can also be employed in the one-step oxidative coupling of 2,4-dialkylphenols:

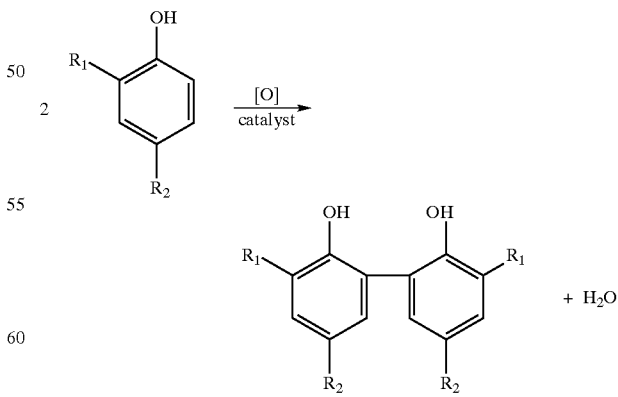

where $R_1$ and $R_2$ are alkyl groups having 3 to 6 carbons. In the case of $R_1$ or $R_2$ having less then 3 carbons, C—O coupling will occur and the process will produce a mixture of C—O coupled oligomers. This reaction does not proceed through the quinone, but otherwise this reaction proceeds under conditions which are substantially the same as those disclosed above for the first stage reaction of the 2,6-dialkylphenol. The reaction is typically conducted using the temperatures, solvents and concentrations described herein for the first stage reaction.

The catalytic system described in this patent can also be employed in the one-step oxidation of 2,2',6,6'-tetraalkyl-4,4'-biphenols.

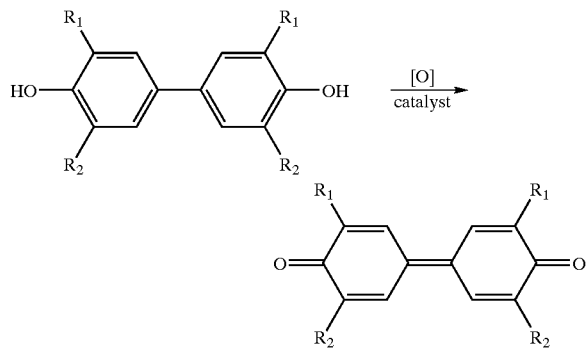

where $R_1-R_2$ are alkyl group having 1 to 6 carbons. The reaction is typically conducted using the temperatures, solvents and concentrations described herein for the first stage reaction. Catalyst may be suspended in the reaction mixture.

While the invention has been described with respect to coupling like dialkylphenols, those skilled in the art will recognize that the invention can also be used to couple dialkylphenols that are different. The latter reaction would merely yield a mixture of products, which could be separated in a conventional manner.

Dealkylation

The products of the reactions described herein can be used directly as antioxidants, UV-absorbers, and specialty monomers. 4,4'-Biphenol can be produced from 2,2',6,6'-tetra-t-butyl-4,4'-biphenol through dealkylation.

Many of the methods of dealkylation that are most commonly known suffer from several major problems, notably the large if not complete loss of isobutylene to form polyisobutylene, an impurity which is very difficult to remove from the final product. Other problems with prior methods of dealkylation include large losses due to alkylation of solvents, long reaction times unless the reaction is conducted at high temperature, and low purity of the 4,4'-biphenol product. These problems can be attributed to the fact that alkylation and dealkylation as well as the polymerization of isobutylene are promoted by the same catalyst in conventional processes.

In accordance with another embodiment of the invention a method of dealkylation is provided which permits essentially complete dealkylation to be achieved at comparatively low temperatures while permitting recovery of more than 90% of isobutylene with high purity, e.g., exceeding 99.5%. The 4,4'-biphenol produced typically has a purity exceeding 99.5% without recourse to further purification by crystallization or distillation.

The method of dealkylation comprises the use of a strong acid and a solvent mixture in which a minimum of one component has a boiling point about 20 to 50° C. lower then the temperature of the reaction mixture. The dealkylation reaction is usually carried out at a temperature of about 130 to 170° C. Examples of the low boiling solvent are hydrocarbons with 7–9 carbons, halogenated hydrocarbons with boiling point about 80 to 130° C. Preferably about 5 to 30% by volume of the solvent mixture is a low boiling solvent. The use of this solvent mixture keeps the reaction mixture saturated with vapors of this low-boiling component and very efficiently removes isobutylene from the reaction mixture before it polymerizes or alkylates the solvent or the biphenols in the reaction mixture. The use of such solvent system also efficiently removes any moisture, which may be present in the reaction mixture. Removing moisture dramatically reduces the reaction time by a factor of two to ten, important for the economics of large-scale production. Examples of acids that can be used in the dealkylation include sulfonic acids such as methanesulfonic acid, which is preferred, sulfuric acid, toluenesulfonic acid, aluminum phenoxides etc.

The invention is illustrated in more detail by the following non-limiting examples.

EXAMPLE 1

Catalyst Preparation: 20 grams of cuprous chloride (CuCl) and 40 grams of tetramethylethylenediamine (TMEDA) are stirred at room temperature in 200 ml of acetone for 3 hours under aerobic conditions (i.e. no attempt is made to exclude atmospheric oxygen). A dark brown solid precipitates and is recovered by filtration, washed with 50 ml of acetone, and dried in the presence of air. 45 grams of catalyst is collected.

EXAMPLE 2

In the three-necked flask equipped with a mixer, a Dean-Stark trap, and a condenser, 424 grams of 2,6-di-t-butylphenol are dissolved at 30 C in 200 ml of methanol. 0.3 gm (0.075%) of catalyst is added. The catalyst rapidly dissolves completely in the reaction mixture. Oxygen is bubbled in the reaction mixture for 3.5 hours at a rate of 150 ml per minute. The reaction is exothermic, so the temperature of the mixture increases from 25° C. to 54° C. in 30 minutes. After 3.5 hours the reaction mixture contains about 35% of 3,3',5,5'-tetra-t-butyl-4,4'-diphenoquinone and about 65% of unreacted 2,6-di-t-butylphenol. Methanol and water are distilled off and the temperature is raised to 150–160 C under nitrogen blanket. After 3 hours at 150 to 160° C., the catalytic oxidative coupling of 2,6-di-t-butylphenol using 3,3',5,5'-tetra-t-butyl-4,4'-diphenoquinone as an oxidizer is complete and reaction mixture contains approximately 70% 2,2',6,6'-tetra-t-butyl-4,4'-biphenol and approximately 30% unreacted 2,6-di-t-butylphenol. The reaction mixture is cooled to 60° C. and 200 ml of the methanol that was previously distilled off is added. The mixture is then cooled to 25° C. and filtered. The filter cake is washed with an additional 50 ml of methanol and air-dried overnight. The dried solids have a mass of 297 grams (70% of theoretical yield of 2,2'6,6'-tetra-t-butyl-4,4'-biphenol). The mother liquor containing 127 grams of unreacted 2,6-di-t-butylphenol and catalyst are reused in the next cycle.

EXAMPLE 3

In a three-necked flask equipped with a mixer, Dean-Stark trap, and a condenser, 404 grams of 2-methyl-6-t-butylphenol are dissolved at 30 C in 300 ml of methanol. 3 grams (0.75%) of catalyst is added. The catalyst rapidly dissolves completely in the reaction mixture. Air is delivered to the headspace of the vessel slowly over a period of 3 days. The reaction mixture is filtered. The filter cake is air-dried, giving 360 grams (89% of theoretical) of 3,3'-dimethyl-5,5'-di-t-butyl-4,4'-diphenoquinone. The mother-liquor contains about 40 grams of unreacted 2-methyl-6-t-butylphenol.

EXAMPLE 4

In a three-necked flask equipped with a mixer, a Dean-Stark trap, and a condenser, 200 grams of 2-methyl-6-t-butylphenol is dissolved in 200 ml of methanol. 1 gram of catalyst is added. The catalyst rapidly dissolves completely in the reaction mixture. 190 grams of 3,3'-dimethyl-5,5'-di-t-butyl-4,4'-diphenoquinone is obtained. Methanol is distilled off and the temperature is raised to 150 C under a nitrogen blanket. After 1 hour at 150° C. the catalytic oxidative coupling of 2-methyl-6-t-butylphenol using 3,3'-dimethyl-5,5'-di-t-butyl-4,4'-diphenoquinone as an oxidizer is complete and the reaction mixture contain approximately 97% 2,2',-dimethyl-6,6'-di-t-butyl-4,4'-biphenol and approximately 3% unreacted 2,6-di-t-butylphenol. The reaction mixture is cooled to 60° C. and 200 ml of the methanol previously removed by distillation is added. The mixture is cooled to 25° C. and filtered. The filter cake is washed with an additional 50 ml of methanol and air dried overnight. The mass of the dried filter cake has a mass of 280 gm (72% of the theoretical yield of 2,2'-dimethyl-6,6'-di-t-butyl-4,4'-biphenol). Additional 100 gm of 2,2'-dimethyl-6,6'-di-t-butyl-4,4'-biphenol along with 10 gm of unreacted 2-methyl-6-t-butylphenol and the catalyst remained in the mother liquor been recovered.

EXAMPLE 5

100 grams of 2,2',6,6'-tetramethyl-4,4'-biphenol (TMBP) of 96% purity is suspended at room temperature in 300 ml of acetone. 1 gm of catalyst is added. Oxygen is delivered to the headspace of the vessel at a rate of 150 ml per minute for a period of 16 hours. The reaction mixture is filtered and the filter cake is dried. 96 grams of 3,3',5,5'-tetramethyl-4,4'-diphenoquinone is collected.

EXAMPLE 6

2000 grams of 2,4-di-t-butylphenol is dissolved at room temperature in 1.5 liters of methanol. 15 grams (0.75%) of catalyst is added. The catalyst rapidly dissolves completely in the reaction mixture. Oxygen is bubbled into the reaction mixture for a period of 3 hours at a rate of 750 ml per minute. The mixture is stirred vigorously at 500 to 800 rpm. The reaction is exothermic, so the temperature increases from 25° C. to 54° C. in 30 minutes. Oxygen delivery is ceased and the mixture is cooled to 29° C. Oxygen delivery is resumed, causing an exotherm that increases the temperature to 54° C. in 30 min. The mixture is stirred for 2 hours at a temperature of 45–46 ° C., then cooled to 35° C. and filtered. The filter cake is washed with 2 liters of methanol, then air-dried overnight. The mass of the dried filter cake is 1,650 grams (82.5% of theoretical yield of 4,4',6,6'-tetra-t-butyl-2,2'-biphenol). The mother liquor is distilled until its volume is reduced to 800 ml, whereupon an additional 85 grams of 4,4',6,6'-tetra-t-butyl-2,2'-biphenol is collected by filtration. The remaining mother liquor containing unreacted 2,4-di-t-butylphenol and catalyst is reused in another cycle.

EXAMPLE 7

In a three-necked flask 50 grams of 2,2',6,6'-tetra-t-butyl-4,4'-biphenol (I) and 0.25 gm of methanesulfonic acid were mixed with a mixture of 80 ml Isopar-G (hydrocarbons $C_{10}$–$C_1$) and 20 ml of toluene. After 2 hours at 150° C., 26 grams of isobutylene is collected in a dry ice trap and the reaction cooled to room temperature and was filtered. The biphenol was dried at 130° C., giving 22.5 gram of 4,4'-biphenol (99% yield) with purity >99% were collected.

EXAMPLE 8

In a three-necked flask, 100 grams of 2,2'-di-t-butyl-6,6'-dimethyl-4,4'-biphenol (1) and 0.25 gm of methanesulfonic acid were mixed with a mixture of 60 ml Isopar-G and 15 ml of isooctane. After 4 hours at 166° C., 27 grams of isobutylene is collected in the dry ice trap and reaction cooled to room temperature and was filtered. 52 grams of 4,4'-biphenol (75% of theoretical yield) with a purity exceeding 99% is collected. Additional amount of 2,2'-di-t-butyl-6,6'-dimethyl-4,4'-biphenol remains in the mother-liquor.

Having described the invention in detail and by reference to specific embodiments thereof, it will be apparent that numerous modifications are possible without departing from the spirit and scope of the following claims.

What is claimed is:

1. A two-step process for preparing tetraalkylbiphenols which comprises: oxidizing a 2,4-dialkyl phenol and/or a 2,6 dialkylphenol with oxygen in the presence of a copper-amino complex to produce a tetraalkyldiphenoquinone, and reducing the tetaalkyldiphenoquinone with a 2,4-dialkylphenol and/or a 2,6-dialkylphenol in the presence of the copper-amino complex to produce the tetraalkylbiphenol.

2. The process of claim 1 wherein the step of oxidizing the 2,4-dialkyl phenol and/or a 2,6-dialkylphenol with oxygen includes dissolving the 2,4-dialkyl phenol and/or 2,6 dialkylphenol in a solvent and bubbling oxygen through the solution or maintaining the solution under a headspace containing oxygen.

3. The process of claim 2 wherein the solvent is methanol.

4. The process of claim 3 wherein the copper-amino complex is prepared by reacting a copper halide and a diamine in a solvent in the presence of oxygen to precipitate the complex.

5. The process of claim 4 wherein the diamine is tetramethylethylenediamine and the copper halide is cuprous chloride or other cuprous compounds.

6. The process of claim 5 wherein the solvent is acetone or tetrahydrofuran.

7. The process of claim 1 wherein the step of oxidizing the 2,4-dialkyl phenol and/or a 2,6 dialkylphenol with oxygen is carried out at a temperature of about 30 to 50 C in the presence of excess dialkylphenol.

8. The process of claim 7 wherein the step of reducing the tetaalkyldiphenoquinone with a 2,4-dialkylphenol and/or a 2,6 dialkylphenol in the presence of the copper-amino complex to produce the tetraalkylbiphenol is carried out at a temperature less than 200° C.

9. The process of claim 8 wherein the dialkylphenol is a 2,6-dialkylphenol and the tetraalkylbiphenol is 2,2',6,6'-tetraalkyl-4,4'-biphenol.

10. The process of claim 9 wherein at least one of the alkyl groups in the 2,6-dialkylphenol contains at least three carbon atoms.

* * * * *